United States Patent [19]

Funke

[11] Patent Number: 4,915,591
[45] Date of Patent: Apr. 10, 1990

[54] RECIPROCATING PUMP AND CONTROL USING OUTLET VALVE POSITION SENSORS

[75] Inventor: Herbert Funke, Krailling, Fed. Rep. of Germany

[73] Assignee: Saphirwerk Industrieprodukte AG, Switzerland

[21] Appl. No.: 191,687

[22] Filed: May 9, 1988

Related U.S. Application Data

[62] Division of Ser. No. 840, Jan. 6, 1987, Pat. No. 4,808,092.

[30] Foreign Application Priority Data

Jan. 8, 1986 [DE] Fed. Rep. of Germany ....... 3600343
Jan. 8, 1986 [DE] Fed. Rep. of Germany ....... 3600342
Jan. 8, 1986 [DE] Fed. Rep. of Germany ....... 3600342
Dec. 5, 1986 [DE] Fed. Rep. of Germany ....... 3641652

[51] Int. Cl.⁴ .................. F04B 49/00; B01D 15/08
[52] U.S. Cl. ................................. 417/18; 417/63
[58] Field of Search ............. 210/198.2; 417/63, 1, 417/18

[56] References Cited

U.S. PATENT DOCUMENTS

| 4,255,088 | 3/1981 | Newton ............................ 417/1 |
| 4,359,312 | 11/1982 | Funke et al. .................... 417/539 |
| 4,420,393 | 12/1983 | Smith ........................... 210/198.2 |
| 4,448,692 | 5/1984 | Nakamoto ...................... 210/198.2 |
| 4,595,495 | 6/1986 | Yofam ........................... 210/198.2 |
| 4,705,459 | 11/1987 | Boisine ............................. 417/63 |
| 4,752,385 | 6/1988 | Wilson ............................. 417/18 |

*Primary Examiner*—Leonard E. Smith
*Assistant Examiner*—D. S. Scheuermann
*Attorney, Agent, or Firm*—Wood, Dalton, Phillips, Mason & Rowe

[57] ABSTRACT

The pump head liner of a small-size precision reciprocating metering pump, which has its application particularly in High Performance Liquid Chromatography (HPLC), is made of transparent material, preferably of synthetic sapphire or monocrystalline zirconium oxide. A pump head casing is designed such that a pump head liner is visually accessible. Cartridge-type check valve units of transparent components are associated with the pump head casing and pump head liner and mounted to be visually accessible. The opening and closing of a ball in a check valve unit can be monitored by an optical sensing system in order to obtain a feed-back signal for governing a control circuitry, having the purpose of compensating the influence of the specific compressibility of the liquid being pumped, upon the pumping efficiency of the displacement system under conditions of high and highest working pressures.

4 Claims, 7 Drawing Sheets

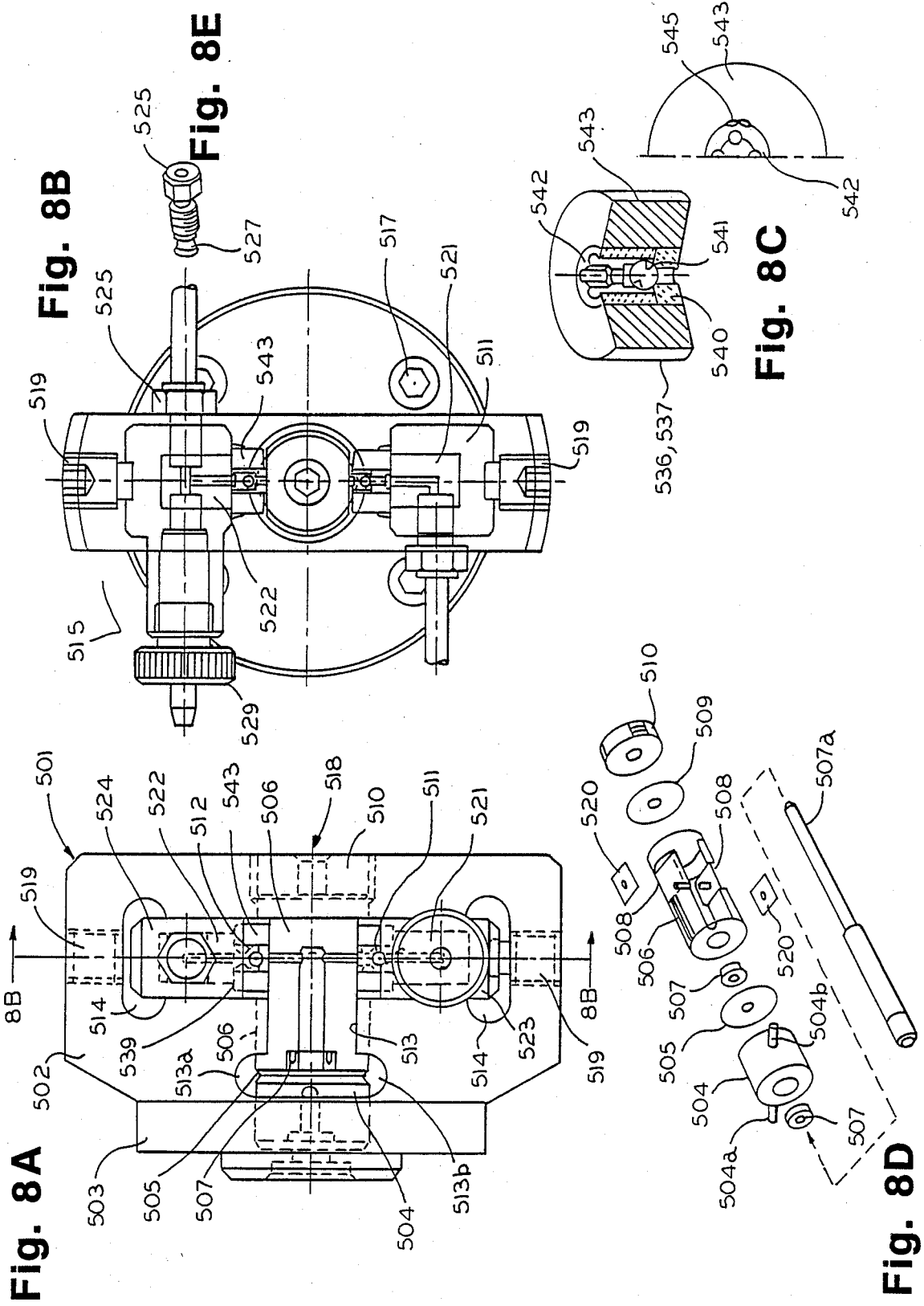

RECIPROCATING PUMP AND CONTROL USING OUTLET VALVE POSITION SENSORS

RELATED APPLICATION

This application is a division of U.S. Ser. No. 000840, filed Jan. 6, 1987, now U.S. Pat. No. 4,808,092 issued Feb. 28, 1989.

FIELD OF THE INVENTION

The present invention relates to a plunger or floating piston pump which is particularly adapted for use as a small-size precision reciprocating metering pump in the field of High Performance Liquid Chromotography (HPLC) techniques. In the pump head casing of said pump at least one pump head liner is inserted having a displacement chamber, as well as inlet and outlet ports and with one piston plunger of clearance fit within each displacement chamber, whereby the pump head liner(s) and piston(s) are made of chemically inert material, and with check valve units of transparent components provided, which are visually arranged in receiving bores of the pump head casing to enable visual sensing for pump control.

BACKGROUND OF THE INVENTION

A pump of said type has been described in U.S. Pat. No. 4,572,056 of the applicant. There it is stated that the pump head liner is to consist of chemically inert material such as the polymers polymonochlorotrifluoroethylene (KEL F) or polyvinylfluoride (PVDF). It is further stated that the pump head liner can also be made of ceramic material for example of aluminum oxide ceramic, which is a polycrystalline material.

The material proposed so far for pump head liners is not transparent and does not permit any view into the displacement chamber for a desired optical inspection of the displacement process. In addition to that, those sections of the pump head liner which are essential for observation are not visible from the outside, but are also covered by the pump head casing. It is particularly important to have the possibility of visual inspection since the delivery volumes of the pump type considered here, which has special application in the HPLC analysis techniques, covers the range of several ml/min to as little as a few microlitres/min and because there is, in addition, a trend towards a miniaturization with regard to the equipment and delivery rate capacity.

SUMMARY OF THE INVENTION

The invention is, therefore, based on the object of improving the known precision reciprocating metering pump in such a way that the displacement process can be observed and monitored from the outside.

This object of the invention is solved in part by the material of the pump head liner being transparent, and in that the pump head casing comprises at least one opening or viewing port through which the pump head liner(s) is (are) visible from the outside.

Visual accessibility of the pump head liner permits the direct optical perception and monitoring of the displacement process. In particular, this entails the possibility of recognizing momentarily and in situ malfunctions due to cavitation (due to formation of liquid vapor bubbles and/or out-gassing of the liquid being pumped in the displacement chamber) originating from gas bubbles sucked into the displacement system via the feeding flow from the liquid reservoir, or because of failing check valves. Furthermore, the piston stroke movement and the condition of the piston seals as well as the extent of wear particle accumulation at the seal and the formation of deposits on the piston can be monitored.

It would be obvious to produce the pump head liner from glass or quartz. The mechanical strength of glass, however, does not suffice by far for the outwardly-acting stress exerted by the hydraulic load of the displaced liquid, combined with the mechanical compression stress exerted within the structure on the pump head liner as a result of the pre-loading compression through the pertinent check valve units. In the type of pump considered here, delivery pressures of up to 600 bar and more occur. A pump head liner of glass, with a desired wall thickness of between 2 to 8 mm, will not withstand such pressure loads.

It is, therefore, proposed to manufacture the pump head liner from synthetic sapphire (which is monocrystalline aluminum oxide) or monocrystalline zirconium oxide and, to polish the surface after its grinding to its final form in order to make the pump head liner transparent. The proposed material withstands an extraordinarily high delivery pressure load. Furthermore, it is chemically inert without restriction, and excludes reliably any trace contamination of the liquid being pumped, which is particularly important in the field of specific biochemical analysis with regard to heavy-metal ion impurities. From this point of view, the choice of material for the pump head liner is very specific. It has in itself an independently inventive importance. Furthermore, the extraordinary hardness of synthetic sapphire and monocrystalline zirconium oxide has the advantage of the pump head liner being scratch-proof, which is important for the durability of the transparency even under continuous rugged operation.

It was even surprising for the applicant, who is specialized in the manufacture of sapphire components, that the material proposed for the pump head liner is suitable even under conditions of highest delivery pressure load, when maintaining wall thicknesses of the displacement chamber which were, until now, typical for polycrystalline zirconium oxide ceramic, which is a special ceramic material having the distinction of possessing a particularly high tensile strength. This surprises even more, because the pump head liner has a complex mechanical stress-inducing T-bore configuration by the central displacement chamber bore in conjunction with the adjacent traverse inlet and outlet port channels. Despite these circumstances, the material withstands the strain of delivery pressures in the range of 600 bar and higher with the desired wall thicknesses of between 2 and 8 mm, preferably 5 mm. Moreover, the same applies even though an additional local compression strain is caused by the pertinent check valve units.

Additionally, it should be noted, that in U.S. Pat. No. 4,572,056, the use of sapphire as the material for the piston is mentioned. The use of sapphire for said piston is, however, not comparable with the pump head liner, since, the piston deals solely with the compression strain of a solid cylindrical body and, synthetic sapphire as the material is selected under the aspect of highest possible wear resistance.

In order to make the transparent pump head liner visually accessible, it is proposed, for a single piston delivery system, to shape the pump head casing like a U-shaped yoke, whereby the pump head liner is arranged in a central dead end bore and is visible through the gap formed by the yoke arms.

Alternatively for a dual piston delivery system having a block-shaped twin-pump head casing, it is proposed to provide the dead end bores for receiving the pump head liners with viewing ports, through which the pump head liners are visually accessible in said receiving bores.

It is already described in U.S. Pat. No. 4,572,056, that the pump head casing can include receiving bores for cartridge-type check valve units, each of which is in contact with the inlet and outlet ports of the pump head liner.

It is not only advantageous to make the pump head liner transparent and visually accessible, but also the check valve units, and have the check valve balls of a different color or opaque. A proposal to bring this idea into effect is that the check valve components excluding the check valve balls are made of synthetic sapphire or monocrystalline zirconium oxide and made transparent by polishing subsequent to final shape-giving grinding and the check valve balls are of ruby. In order to have the check valve units visibly accessible from the outside, the pump head casing can be provided with interstices or viewing ports.

A further aspect of the present invention relates to a plunger or floating piston pump which is particularly adapted for use as a small-size precision reciprocating metering pump in the field of HPLC techniques, featuring a pump head casing comprising at least two displacement chambers, which are connected to check valve units via inlet and outlet ports, and, with one piston for each displacement chamber. At any given time at least one piston performs its displacement stroke. A pre-compression stroke is carried out prior to each such displacement stroke in order to compensate for the influence of the specific compressibility of the liquid being pumped on the pumping efficiency of the delivery system. Further, a piston position indicator and a sensor device monitoring the actual onset of liquid displacement, are both connected to a speed control circuitry.

Precision metering pumps of said type are known and described for example in the U.S. Pat. No. 4,359,312. The present invention thereby, relates not only to versions of such type of pump where the outlet ports of the pertinent displacement systems are connected in parallel, as described in the above cited patent specification, but the same in principle, to versions of such type of pumps, where the pertinent displacement systems are connected in series as assemblies, with only one of them being fitted with check valve units, as described by functional concept in the German Patent Specification No. 3203722. It is the objective of said type of pumps to obtain a pulse-free liquid mass flow. This is achieved in that, each displacement system performs prior to the displacement stroke a pre-compression stroke generated by a corresponding profile section on the actuating cam for the piston being set for a chosen maximum of delivery conditions. In case actual delivery pressure and specific liquid compressibility conditions do not demand the use of the complete length of the pre-compression stroke which is mechanically set on the side of the cam, the drive motor speed is controlled in such a way for the cycle of the residual pre-compression stroke profile not to be utilized for the defined purpose, that a constant composite flow is produced by both pistons. In order to be able to apply precise pre-compression during continued pumping operation, it is necessary to precisely determine the onset of the actual liquid displacement. In case of the precision metering pump according to U.S. Pat. No. 4,359,312, this is effected by means of monitoring the delivery pressure. This mode of obtaining a function cycle monitoring signal, however, is technically difficult, in particular because the liquid being pumped can be subjected in the displacement chamber to pressure fluctuations caused by internal or external artifacts and, therefore, a cycle-time window and a threshold has to be set for the characterization of the pressure change to be significant.

This aspect of the invention is, therefore, based on the objective of achieving for a pump of the above type a design which allows precise determination of the moment of the actual onset of the liquid displacement and by that an improved feed-back control of the drive system.

The objective of the invention is solved by means of a sensor device which monitors the opening cycle of at least one outlet check valve unit.

When using check valve units according to the ball and seat principle, the solution according to the invention is embodied in that, said sensor device is triggered by the lifting of the ball from its seat.

A preferred embodiment is that at least one outlet check valve unit comprises in part transparent components, with a check valve ball however, which is colored or opaque, and that the sensor device monitoring the actual onset of the liquid displacement, is an optical system as, for example, a light-gate which is triggered by lifting of the ball from its seat by interference with the light beam or by alteration of the refractive index conditions in the ball area.

A transparent outlet check valve unit offers the advantage of optical-electronic monitoring and visual accessible installation in the pump head casing for inspection from the outside.

Sapphire and monocrystalline zirconium oxide in transparent configuration of the parts made thereof, are particularly suitable as material for a transparent check valve unit. These materials are not only transparent, they are also virtually chemically inert and extremely hard, thus ensuring high wear and scratch resistance. The check valve ball can, for example, be made of ruby which is of red color and, thus, allows reliable optical monitoring of its movement within the check valve unit during pumping operation.

A further possibility consists of making the ball of at least one check valve unit from a ferro-magnetic material, preferably special stainless steel. In this case, the onset of the actual liquid displacement can be detected by magnetically monitoring the movement of the check valve ball. Further, the use of sapphire or monocrystalline zirconium oxide for the peripheral components of the check valve unit is favorable with regard to this, since said materials are nonmagnetic and, thus, exhibit no magnetic shielding effect.

Alternatively, it is also possible to make the check valve ball of ferro-magnetic material and to coat the ball with a ceramic material, such as titanium carbide, which is chemically inert and extremely hard.

The previously described check valve units, which are transparent and whose inspections is possible from the outside, can be monitored by an optical sensing device, such as a light-gate which responds to the functioning of the check valve unit, in particular to the lift-off of the check valve ball from its seat. Such optical monitoring benefits from the fact that the check valve ball is in a different color than the other check valve components when made of ruby. The optical sensing device or light-gate can be used in feed-back control circuitry to determine when liquid displacement effectively starts and by means of said control circuitry the piston velocity is controlled for the purpose of compensating for the influence of the specific compressibility of the liquid being pumped on the pumping efficiency as a function of the delivery pressure in the displacement chamber.

So far, actual displacement onset values were derived by monitoring the working pressure within the displacement chamber. To obtain pressure values for this purpose is, however technically difficult, in particular because the liquid being pumped is subjected to pressure fluctuations within certain tolerance limits in the displacement chamber, which allow a valid measurement of the actual displacement onset only when a change of pressure exceeds a tolerance threshold. The lifting of the check valve ball from its seat in the check valve unit can, in contrast, be clearly detected and is optically determinable. The idea of optically determining a value for the actual onset of the displacement process for the purpose of using it in a feed-back control circuitry to compensate for the effect of the specific compressibility of the liquid being pumped on the pumping efficiency as a function of the working pressure is regarded as being of an independently inventive importance.

In order to allow better inspection of the displacement process and the stroke movement of the piston in the displacement chamber, it is proposed, as is already known, to provide the piston, which consists of synthetic sapphire, with a light source at its clamping end or ferrule. This light source can, for example, be a light emitting diode. Alternatively, it is possible to provide the pump head casing with at least one bore hole which leads to the bore section(s) enclosing the pump head liner(s) and which serves to receive the light source which illuminates the pump head liner(s).

In summary, the advantages are once more stated which are achieved by the transparency of the pump head liners and of the check valve units as well as of the visual accessibility of said pump components. A direct monitoring of the functioning of the check valve units and of the piston's movement as well as the condition of the piston seal is ensured. This again enables detection of cavitation or of the retention of air bubbles sucked into the displacement chamber by the feeding liquid flow of the pump.

Finally, it is possible to obtain an optical-electronic control signal for the feed-back regulation on the piston velocity with the purpose of compensating for the influence of the specific compressibility of the liquid pump upon the pumping efficiency of the delivery system at high and highest possible delivery pressures.

BRIEF DESCRIPTION OF THE DRAWING

FIG. 8A is a view, similar to FIG. 7A, with parts shown in greater detail;

FIG. 8B is a section, taken generally along line 8B—8B in FIG. 8A;

FIG. 8C is a perspective sectional view and a partial plan view of a check valve cartridge;

FIG. 8D is an exploded view of the pumping components;

FIG. 8E is a perspective view of a component of the pump illustrated in FIG. 8B;

DESCRIPTION OF THE PREFERRED EMBODIMENTS

Figures 1, 2:
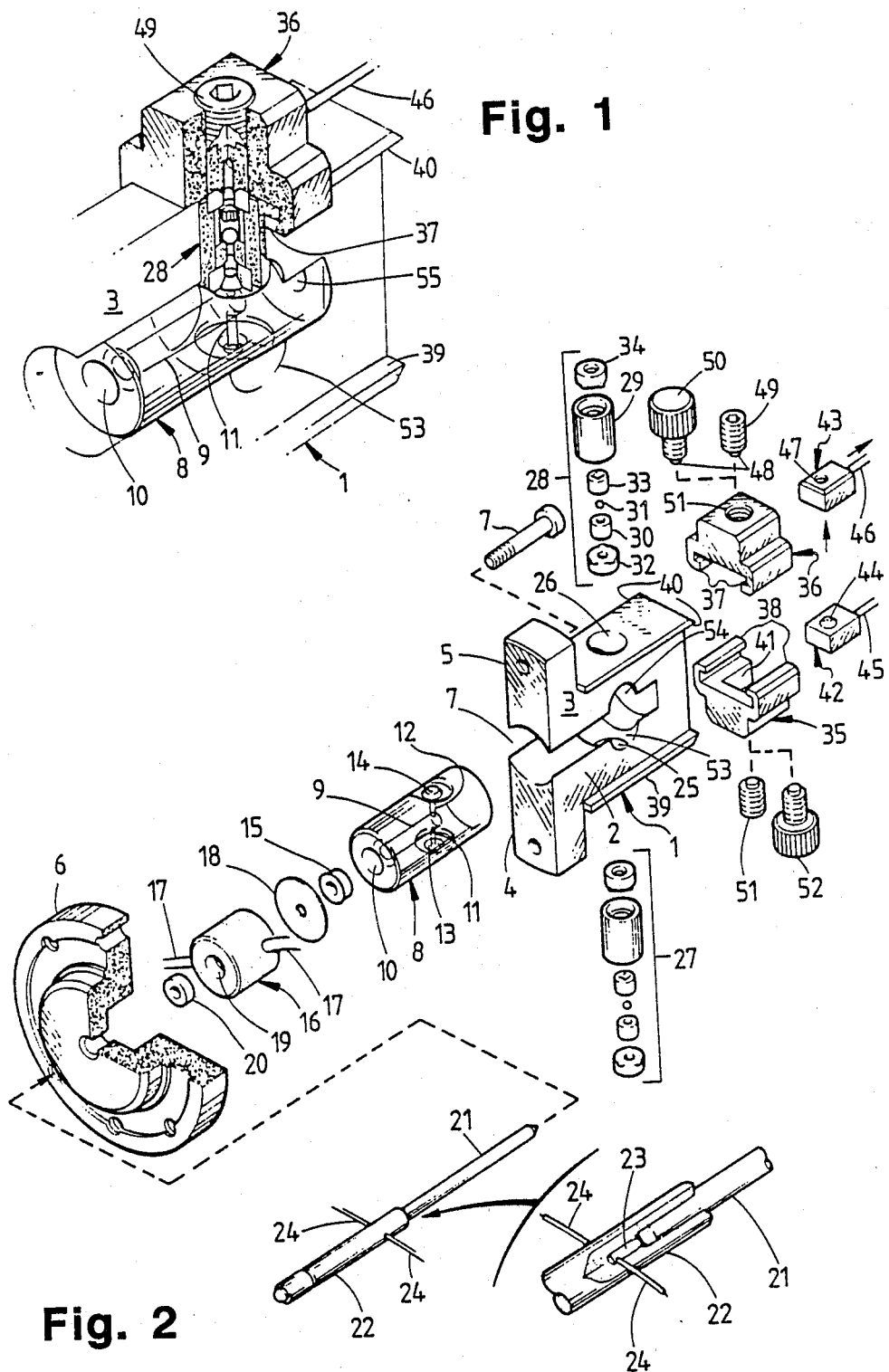
FIG. 1 is a perspective section through the first configuration of the small-size precision reciprocating metering pump.
FIG. 2 is an exploded view of the small-size precision reciprocating metering pump of FIG. 1.

The small-size precision reciprocating metering pump shown in FIGS. 1 and 2 displays a pump head housing 1 which takes the form of a U-shaped yoke. The arms of the yoke are numbered 2 and 3. There are flanges 4 and 5 at the free ends of the yoke arms 2 and 3 for the attachment of the pump head yoke to a mounting shield 6 by means of screws 7. The pump head housing 1 and the pump head mounting shield 6 are made of stainless steel or chemically resistant polymer. The gap between the yoke arms 2 and 3 forms a laterally open dead-end bore and serves to receive the pump head liner 8.

The pump head liner 8 is made of synthetic sapphire (monocrystalline aluminum oxide) or monocrystalline zirconium oxide. In their raw state, said materials are clear or transparent. In order to make the pump head liner out of said materials, however, they must be ground to shape, from a solid raw piece, by which action it becomes opaque. By subsequent polishing, it turns transparent again. Sapphire and monocrystalline zirconium oxide are chemically inert and exceptionally hard and, therefore, are scratch-proof, even during continuous rugged operation. The pump head liner features an axial dead-end bore displacement chamber 9 which, at the open end, widens out into a collar groove 10. A traverse inlet port 11 and traverse outlet port 12 lead to the base of the dead-end bore of the displacement chamber 9. The pump head liner features small annular rims 13,14 which surround the port channels on those positions where the inlet port 12 and outlet port 11 meet the mantle surface of the pump head liner 8. Furthermore, the flat ground surfaces adjacent to said rims are excluded from polishing and deliberately left coarse.

The wall thickness of the pump head liner can be maintained relatively thin, when choosing said materials in spite of the high delivery pressures which are common in HPLC techniques. It can, for example, be between 2 and 8 mm, preferably 5 mm, nonetheless; such a pump head liner can withstand delivery pressures of up to and above 600 bar.

The collar groove 10 serves for the reception of a spring-loaded annular piston seal 15, which is made of, for example, PTFE.

The gap between the two yoke arms 2 and 3 of the pump head casing 1 is foreseen furthermore to accept a piston guide bushing 16 which can be made of ceramic material, such as sintered aluminum oxide, and which is fitted with flushing and draining connection tube segments 17. A PTFE film washer seal 18 is inserted between the piston guide bushing 16 and the pump head liner 8. The piston guide bushing 16 is furthermore provided with a collar groove 19 at the opening opposite the pump head liner 8. Said collar groove 19 serves for the reception of a spring-loaded annular piston seal 20. The seals are peripheral sealing elements for the case that continuous or discontinuous flushing is applied to the piston guide bushing when pumping salt-containing buffers which tend to produce crystals on the piston surface within the stroke area.

A piston 21 made also of sapphire is permanently slidably guided through the piston guide bushing 16. The piston 21 is not in contact with the wall of the displacement chamber 9 of the pump head liner, but has a clearance fit. The piston 21 is clamped into a ferrule 22 which is connected to a drive mechanism (not shown here). A light diode 23 is installed in the ferrule 22, connected to an electrical supply by conducting wires 24. The light emitting diode 23 emits light into the piston 21, made of transparent sapphire, as a result of which the pump-head liner 8 is illuminated from the interior.

The two yoke arms 2 and 3 of the pump head casing 1 are further provided with bores 25,26, which extend vertically to the axes of the pump head liner 8. The bore 25 serves to receive a cartridge-type inlet check valve unit 27, the bore 26 serves to receive a cartridge-type outlet check valve unit 28. Both check valve units have the same internal components, the arrangements of which differ according to the inlet or outlet configuration. It is sufficient, however, to describe the outlet check valve unit 28.

The outlet check valve unit 28 comprises a bushing-type cartridge housing 29, which encloses a ball guide/ball stopper element 33. A check valve ball 31 is slidably arranged in said element. On its open end, said element butts onto a sapphire valve seat 30. The closed end of the ball guide/ball stopper element 33 is sealed off by a cross cut or sieve-plate profile section. Both openings of the check valve cartridge housing 29 enclosing the ball guide/ball stopper element 33 and the check valve ball 31 together with its seat 30 are closed by annular seals 32, 34. The check valve cartridge housing 29 and the ball guide/ball stopper 33 as well as the seat 30 consist of transparent material, preferably of the same material as the pump head liner 8, i.e. of synthetic sapphire or monocrystalline zirconium oxide. The check valve ball 31 is made of ruby. It is red and, therefore, clearly distinct from the aforementioned mating components. The two annular seals for the peripheral sealing as well as for an assemblage of the inner check valve components in the cartridge housing are made of PTFE.

The two yoke arms 2,3 of the pump head casing 1 are provided with interstices 53,54 which allow visual accessibility of the check valve cartridge section which houses the ball guide/ball stopper element 33 and the check valve ball 31 as well as the seat 30. Thus, the movement of the check valve ball 31 in the outlet check valve unit 28 within the ball guide/ball stopper element 33 and onto and from the seat 30 is clearly visible via said interstice 54. The annular seal 32 is positioned on the coarse surface of the pump head liner 8 adjacent to the seal-bore backing rim 14. In order to secure the cartridge-type check valve units 27,28 within the receiving bore holes 25,26, clamping brackets 35,36 are provided. On the bracket ends are ridges 37,38 which form internal grooves. The pump head casing 1, in turn, has a double-T profile relative to the cross-axis of the pump head liner 8. The two clamping brackets 35,36 are slid with their internal grooves along the mating edges 39,40 of the pump head yoke for locking.

Furthermore, the clamping brackets 37,38 feature on their cross-bar an internal interstice (shown only for clamping bracket 35 as detail 41 in FIG. 2), in which the adapter pieces 42,43 for the connecting tubes are slidably received, set and locked in position.

The adapter pieces 42,43 feature an elbow-shaped liquid duct which is surrounded by an annular rim at the opening which penetrates to the side facing the adapter piece and which is, at its other end, joined to a connecting tube for the liquid being pumped. For the adapter piece 42, the annular rim is numbered 44 and the connecting tube 45. At the adapter piece 43, the annular rim is not visible; the connecting tubes here is numbered 46. The path of the liquid being pumped in the adapter piece 43 which is connected to the outlet check valve unit is indicated by arrows. The adapter piece 43 reveals an indentation, recess hole 47, which is opposite to the side of the pertinent check valve unit 28 into which a round-tipped plug 48 of a grub screw 49 or a knurled-head screw 50 can engage.

The grub screw 49 or the knurled-head screw 50 are screwed into an open-end threaded bore 51 which is provided in the clamp bracket cross-bar. The grub screw 49 or knurled-head screw 50 are foreseen as compression elements for the purpose of a leak-free assembly of the adapter piece 43, the outlet check valve unit 28 and the pump head liner 8. Similarly, a grub screw 51 or a knurled-head screw 52 is provided for clamping bracket 35. The use of grub screws or knurled-head screws enables a particularly sensitive attachment of the check valve cartridges which permits peripheral sealing without an excessive mechanical pre-loading of the check valve units relative to the pump head liner. As a result of inserting an adapter piece tightly set and locked in the pertinent clamping bracket, furthermore eliminates the transfer of rotational motion from the screws to the check valve cartridges. This is important since the peripheral sealing at the interface areas is obtained by means of flat seal elements, which optimally should be pre-loaded only by axially acting force. The flat seal 32 of the outlet check valve unit 28 and the corresponding flat seal of the inlet check valve unit 27 face the pump head liner on unpolished, i.e., purposely coarsely-ground contact surfaces. A twisting of the flat seals on these contact surfaces during the tightening process would interfere with the desired wedging of the adjacent surfaces in microscopic dimensions. The use of adapter pieces avoids the conventional small size fitting connections (fitting screw and ferrule) which tend to leak due to plastic deformation of the ferrules after repetitive tightening and loosening.

In the previously described small-size precision reciprocating metering pump, the pump head liner 8 is visibly accessible through the gap between the yoke arms 2 and 3 of the pump head casing 1. Since the pump head liner 8 is made of transparent material, the stroke movement of the piston and the delivery process can be observed, in particular, the occurrence of cavitation and-/or the presence of air bubbles which reach the displacement chamber 9 via the feeding flow of the pump is discernible. Furthermore, the condition of the piston seal and the extent of the generation of seal wear and the accumulation of deposit on the piston surface are also visible.

In addition, the function of the check valve units 27,28 can be visually monitored via the interstices 53,54. The visual monitoring is facilitated by the illumination of the pump head liner 8 via the piston 21. Instead of illuminating piston 21, it is also possible to provide a bore hole 55 (see FIG. 1) in the arc section of the pump head yoke casing 1 into which a light source is installed (not shown here).

Figure 3:
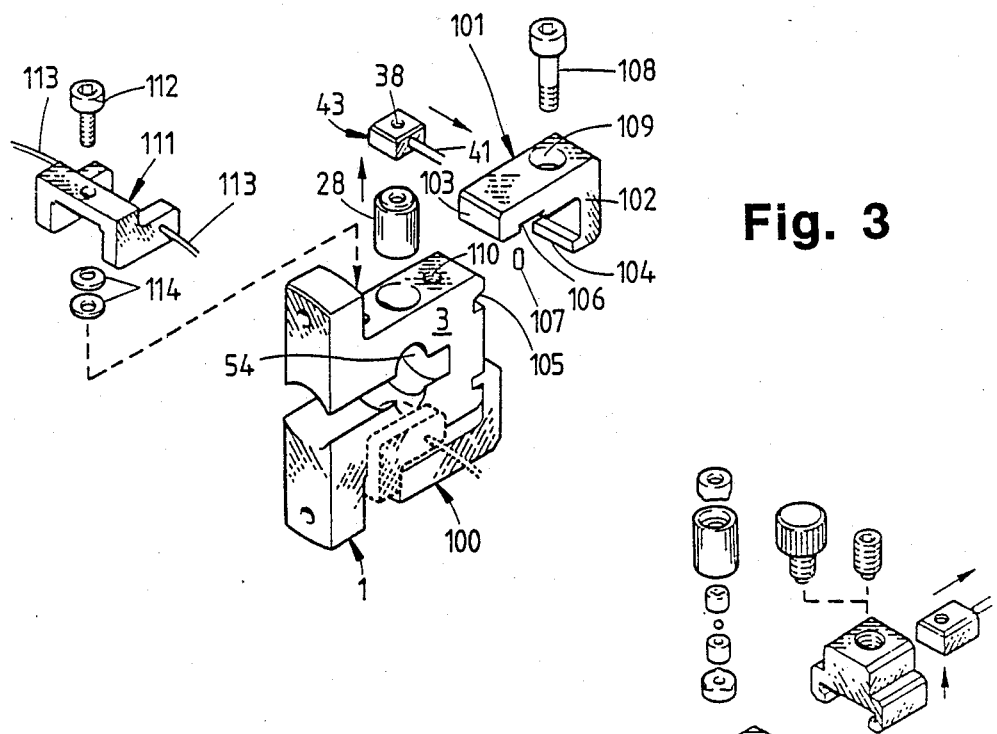
FIG. 3 shows the essential components of a second configuration of small-size precision reciprocating metering pump in exploded view.

In the second configuration as shown in FIG. 3, the small-size precision reciprocating metering pump of the invention is provided with L-shaped angled clamps 100,101 instead of the clamping brackets. Since the L-shaped angled clamps are identical in shape, only clamp 101 will be described in more detail. Said clamp consists of a supporting arm 102 and a clamping arm 103. A protrusion 104 is provided on the supporting arm 102 which engages into a frontal slot 105 on the pump head yoke casing which has also been assigned number 1 here. In order to receive the adapter piece 43, whose connecting tube 41 is facing sideways in this case, a slot 106 is provided in the clamping arm 103. A pin 107 is set firmly in the clamping arm 103, the free end of which is rounded. The rounded end of the pin 107 engages into the cut-out hole 38 on the adapter piece 43. The clamping here is effected indirectly by means of a compression screw 108 which passes through a bore 109 in the clamping arm 103 of the L-shaped angled clamp 101 and which is screwed into a bore 110 in the pump head yoke casing 1. The configuration according to FIG. 3 is new in respect to configuration 1 and 2 in that a saddle bracket 111 is screwed onto the upper yoke arm of the pump head casing 1 by means of a screw 112. This saddle bracket 111 contains a light-gate (not visible) which monitors the movement of the check valve ball in the transparently held outlet check valve unit 28 though the interstice 54 in the yoke arm 3 of the pump head casing 1. The transmission and reception of light to and from the light-gate is effected via fiber-optic cables 113. The light-gate can, of course, be embodied by a light emitting diode in conjunction with a photocell.

Spring washers 114 are inserted between the saddle bracket piece 111 and the upper yoke arm 103 of the pump head casing 1. This enables the adjustment of the height of the saddled bracket piece 111 by gentle or firm tightening of the screw 112 such that the light-gate crosses the path of movement of the ball in the check valve unit 28 precisely.

By means of the light-gate an opto-electronic or optical-electronic signal can be derived for a feed-back control circuitry which compensates for the specific compressibility of the liquid being pumped at high and highest possible delivery pressures. It is equally possible to detect the, movement of the ball in the check valve unit 28 in a different way, for example, by an electric or magnetic sensor, as seen in FIG. 6A. In this case, the ball 31a would have to be made of metallic material, such as steel, and be coated appropriately for achievement of chemical inertness. As seen in FIG. 6A, the movement of the ball 31a can be sensed by a magnetic sensor 31b of a type well known in the art.

Figure 4:
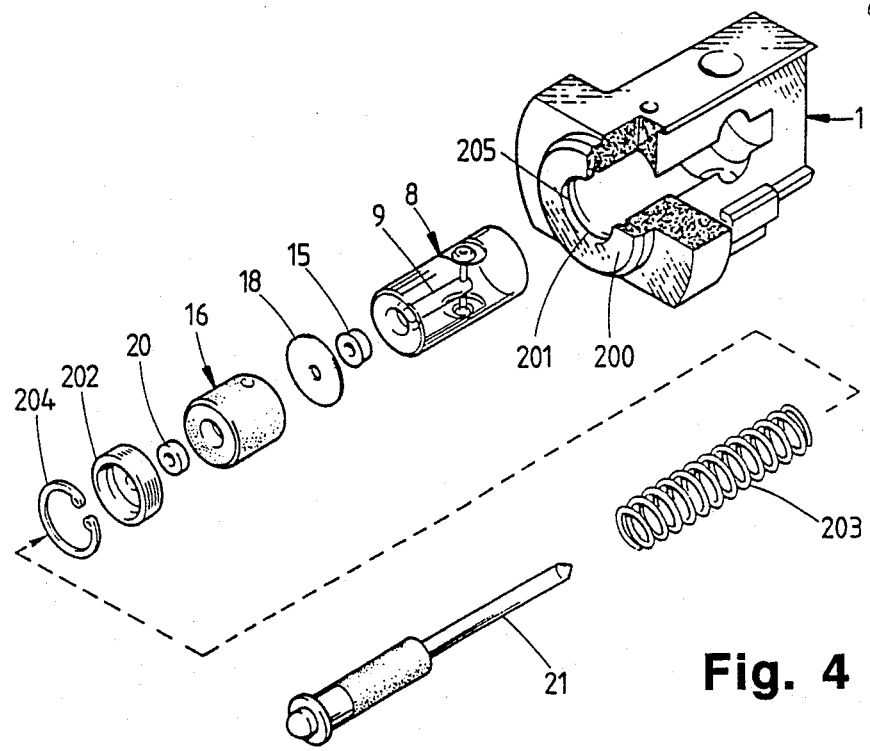
FIG. 4 shows a third configuration of small-size precision reciprocating metering pump in exploded view.

The third configuration according to the invention as shown in FIG. 4, differs from the configuration according to FIG. 1, in that the pump head mounting shield 200 and the pump head casing 1 are one piece. The pump head mounting shield 200 contains an receiving bore 201 into which the pump head liner 8 with the piston seal 15, the sealing washer 18 and the piston guide bushing 16 with its seal 20 can be inserted. In addition, a counter-support 202 for the returning spring 203 of the piston is positioned in said receiving bore 201. The above mentioned parts are held in place by means of a slip ring 204, which is inserted into another groove located in the bore 201 of the pump head mounting shield section 200 of the pump head casing 1.

Figure 5:
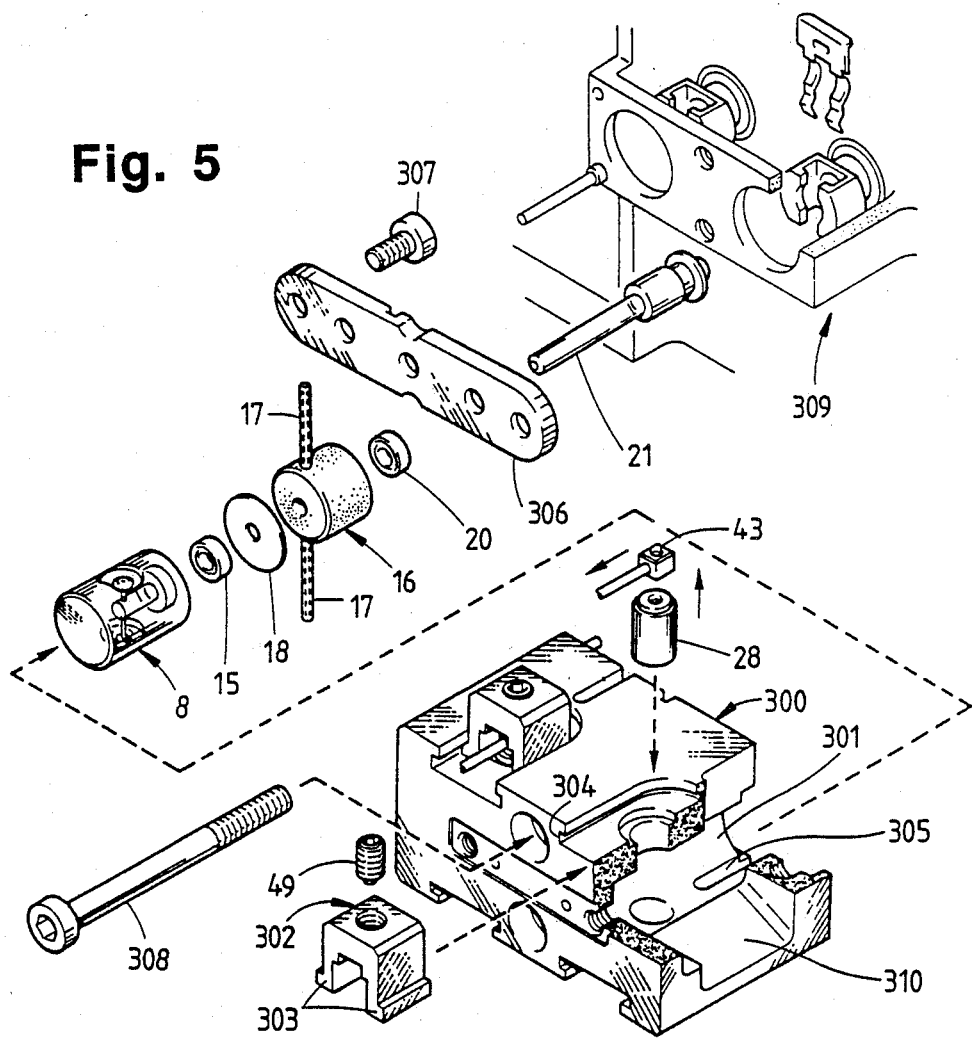
FIG. 5 shows a fourth configuration of small-size precision reciprocating metering pump as a dual-piston displacement system in exploded view.

The fourth configuration according to the invention as shown in FIG. 5 presents the small-size precision reciprocating metering pump as a dual-piston system. The pump head casing 300 is block-shaped in this case and it is provided with two receiving bores for each of the pertinent pump head liners 8. Only receiving bore 301 is shown, the check valve units are secured in the pump head casing 300 completely analog to the mode shown in FIGS. 1 and 2. The check valve unit 28 and the adapter piece 43 are shown. Both these parts are pressed together and in assembly against the pump head liner 8 by means of a clamping bracket 302 and the grub screw 49. In contrast to FIG. 1, the ends of the clamping brackets 302 feature external ridges 303 in said configuration and engage into grooves 304 on the pump head casing block 300.

The pump head casing block 300 is provided further with slots 305 for the flushing or drainage connecting tube segments 17 which lead to and from the piston guide bushing 16. The parts inserted into the receiving bore 301 are secured by means of the cross-bar 306 mounted onto the pump head casing block 300 with screws 307. Additional screws 308 pass through the pump head casing block 300 in order to fasten same to a driving unit 309 for piston 21.

The pump head liners 8 are visually accessible, as shown in FIG. 5, by inwardly tapered viewing slots 310 on the sides of the pump head casing block 300. A visual accessibility to the pertinent check valve units is not intended here, but it would be feasible to do so.

The peripheral components in the case of all four configurations are made from stainless steel. If exceptional chemical inertness is required, the adapter pieces 42,43 and the check valve cartridge housings being in contact with the liquid being pumped can be made of titanium or tantalum. The same applies to the connecting tubes 45,46. If not, check valve units are used which are fitted with chemically inert inserts covering all wetted parts and liquid ducts, in conjunction with PTFE pressure hose in order to achieve a complete inlet to outlet non-metal configuration of the displacement system. The clamping brace 100,102 can be made of stainless steel or chemically resistant fiber-reinforced polymer. The latter can be produced by injection-molding. Same applies to the pump head casing.

Figure 6:
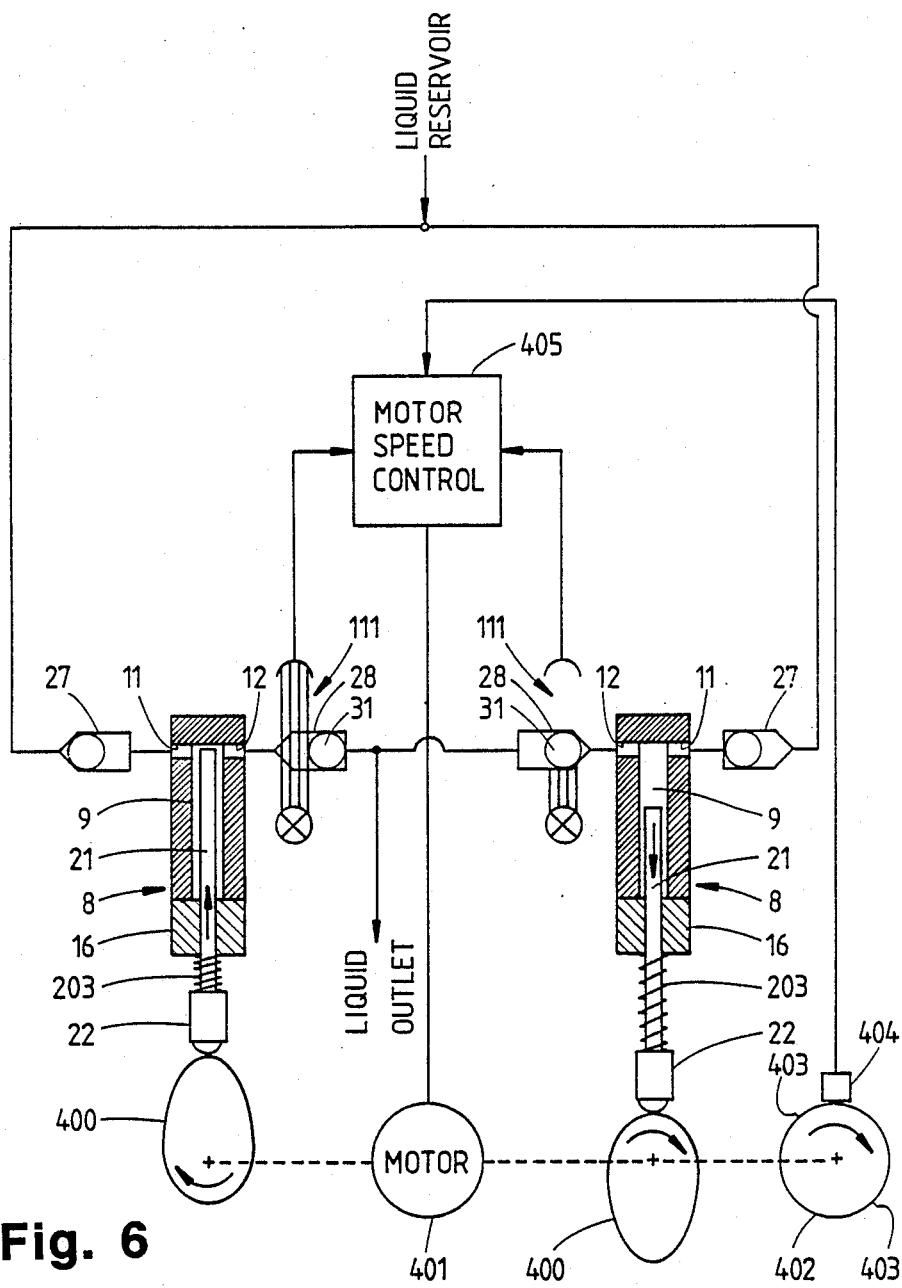
FIG. 6 is a block circuit diagram of a dual-piston displacement system with feed-back control for the compensation of the influence of liquid compressibility on the pumping efficiency of the displacement system.
Figure 6A:
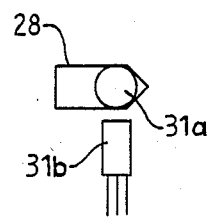
FIG. 6A is a fragmentary view of magnetic sensing structure.

The dual-piston displacement system according to FIG. 6 shows two pump head liners 8. The inlet check valve unit 27 of the one pump head works together with the outlet check valve 28 of the other pump head in alternating cycle during the displacement process. The pistons 21 of the two pump head liners are driven by cams 400 in such a way that, with a certain cycle overlap, one-pump head delivers whilst the other refills. The kinematic profile of the cams 400 is designed in such a way that each piston 21 performs a pre-compression stroke prior to the actual, normal delivery displacement stroke. This is in order to compensate for the flow-drop accompanying the onset of the actual displacement stroke at elevated working pressures due to the specific compressibility of the liquid being pumped, leading to the residual pulsation of the delivered flow. The underlying liquid compressibility compensation concept is described in more detail in U.S. Pat. No. 4,359,312.

Both cams 400 are driven by means of motor 401 whose rotational speed is controlled by speed-control device 405. This device is connected both to the optical-sensor device 111 hooked to the outlet check valve unit 28 and to piston position indicator 404. The piston position indicator 404 scans transmitter wheel 402 which is mounted onto the common axle for motor 401 and cams 400 and which features two peripherally and diametrically opposed pins 403. Said pins are arranged on transmitter wheel 402 in such a way that they trigger piston position indicator 404 at the onset of each pre-compression stroke. Parallel to this, speed control device 405 receives signals from optical sensor device 111 when displacement of liquid from displacement chamber 8 actually begins. In this instant, the ball of check valve unit 28 lifts from its seat and triggers the monitoring system of optical sensor device 111. From the time difference between the mechanical and the hydraulic onset of the displacement process, speed control device 405 computes the necessary pre-compression and, for any residual pre-compression cam profile section not being used for pre-compression, corrects the motor speed in such a way that a composite constant flow is generated for said cam profile section by both pistons. In addition, speed control device 405 simultaneously compensates for the additional flow, generated by the pre-compression mode, relative to volume at atmospheric pressure, by means of superimposing a corresponding correction factor to the rotating speed. By this procedure, a constant pulse-free liquid-mass flow is obtained.

The optical sensor device 111 (light-gate) can be, as shown, a light-source in conjunction with a light-sensor element oppositely arranged to each other, with the check valve unit in between. Such an arrangement functions according to the light-beam interference principle. An alternative configuration, working according to the refractive principle has a light-source and light-sensor element arranged on the same side of said check valve unit (not shown), being triggered by the alteration of the refractive conditions in the check valve area due to its opening and closing movement.

The fifth configuration of the pump head unit is shown in FIGS. 7A–7B, 8A–8D, 9A and 9B and combines a single-piece integral design having a pump head mounting shield 503 and yoke-shaped pump head body. This design obsoletes separate fixing elements for the check valve assemblies which are submodules. The annular flange or mounting shield 503, integral with the yoke-shaped pump head body 502, features recessed bore-holes 516 for fixing screws 517 intended for mounting the pump head to the corresponding drive unit (not shown).

The actual pump head casing 501 is formed by a slim and particularly high yoke-body 502 having a central recessed bore 518 which is accessible from the front and serves to accept the transparent pump head liner 506 and the ceramic piston guide bushing 504. In order to make said two parts visually accessible, the yoke-shaped body is horizontally slotted to define spaced yoke arms and to form viewing ports 513. At their rear base, these ports widen to a T-shape having sections 513a and 513b in a way that oblique alignment of the flush tubes 504a and 504b on the piston guide bushing is feasible.

The front end of the central recessed bore 518 in the yoke-shaped body 502 which features no cut-outs, is threaded for accepting a ring screw 510 with a central hexagonal bore. This screw is intended to fix the piston guide bushing 504 and the pump head liner 506 in the yoke-shaped body receiving bore 518, with a PTFE film washer 505 in between which functions as a peripheral sealing element in connection with the piston guide bushing which can be externally flushed. An identical washer 509 is positioned between the pump head liner 506 and the fixing ring screw 510 as a kind of buffer element, ensuring uniform distribution of axially acting forces, exerted on the front side of the pump head liner due to slight pre-loading of the insert parts on the one hand, when mounting them adjacently to each other, and on the other hand, as a consequence of the hydraulic load during the pumping operation under condition of high and highest working pressures. A pair of seals 507 are associated with the piston 507a which is reciprocal in the pump head liner 506.

Additionally to the above described horizontal viewing ports, the yoke-shaped body of the pump head is penetrated on both sides by I-shaped, vertical slots 514 formed in the yoke arms. These slots cross said viewing ports at their front base. The resulting crossing area is dimensioned to allow the piston guide bushing 504 to be inserted sideways into the central recessed bore of the pump head yoke-shaped body. This provision is necessary because the flush tubes 504a and 504b on the piston guide bushing 504 do not permit a mounting via the laterally closed front opening.

The vertical slots 514 described before serve as viewing ports as well as cut-outs for sideways mounting of the modular check valve assemblies 511,512. Sealing force (pre-loading) is effected by pressing them against the pump head liner 506 by grub screws 519 which are threaded in the arches above and below said vertical slots 514.

The pump head liner differs from the other configurations of the invention in one detail. There are no backing rims around the capillary inlet and outlet port bores. These rims in the other configurations are intended as a peripheral backing protrusion for preventing a possible deformation of the mating annular seal made of reinforced PTFE (this material is chosen for the reason of offering appropriate chemical inertness, but at the same time strongly tends to cold-flow under the pre-loading force applied on the check valve assemblies in order to obtain liquid-tight sealing). The improvement in this embodiment results because only extremely thin PTFE washer-type flat seals 520 are used as peripheral sealing elements. For receiving said washer-type flat seals, the modified pump head liner features simple flat cut-outs 508 at the inlet and outlet port bores as mating surfaces for the check valve unit modules 511,512. These cut-outs are square when viewed from the top, and by this correspond to the shape of the pertinent flat seals, which are slightly oversized in order to ensure selfholding against rotation when applied to the receiving cut-outs on the pump head liner.

Use of very thin washer-type peripheral sealing elements eliminates the problem of cold-flowing check valve sealing rings. Also, they reduce the dead volume in the displacement system affecting pumping efficiency, since the critical volume area with regard to this, ranges from the sealing edge of the inlet check valve to the sealing edge of the outlet check valve seat.

The modular check valve assemblies 511,512 are characterized in that:

(1) All components whose surfaces are wetted by the liquid being pumped are either made from sapphire and ceramics or of chemically inert polymer materials. Also, no contact with metallic surfaces is given within the interface areas between the check valve assemblies and the pertinent liquid connecting tubes.

This is achieved, in principle, by means of a chemically inert polymer liner 521,522, press-fitted into a center bore-hole of the check valve module body 523,524 and in this location covers all areas wetted by the liquid being pumped.

(2) The feature "fitting-less check valve unit" (which means by its very nature that the connecting tubes must not be separated from the unit for the purpose of removal from the pump head and a possible subsequent disassembly as well as no transfer of rotational force on the unit when sealing force is applied) and the feature "separable connecting tubes" are combined with each other.

This is achieved in that the check valve unit modules 511,512 can be inserted sideways into the corresponding receiving slots 514 with no possible interference of the connecting tubes. Additionally, there is no transfer of rotational force on the check valve unit modules when applying sealing force by means of the pertinent compression grub screw 519 in order to obtain liquid-tight sealing in conjunction with the pump head liner 503. Pre-loading forces merely act axially on the washer-type seals 520 due to the receiving slots 514 having a rectangular cross-sectional shape congruent to the check valve unit module casings 523,524. Further, the tip of the compression grub screw 519 engages into a mating recessed bore-hole on the back side of the check valve module body 523,524 in a way that correct alignment of the whole check valve unit/pump head liner assembly is achieved.

Figure 7B:
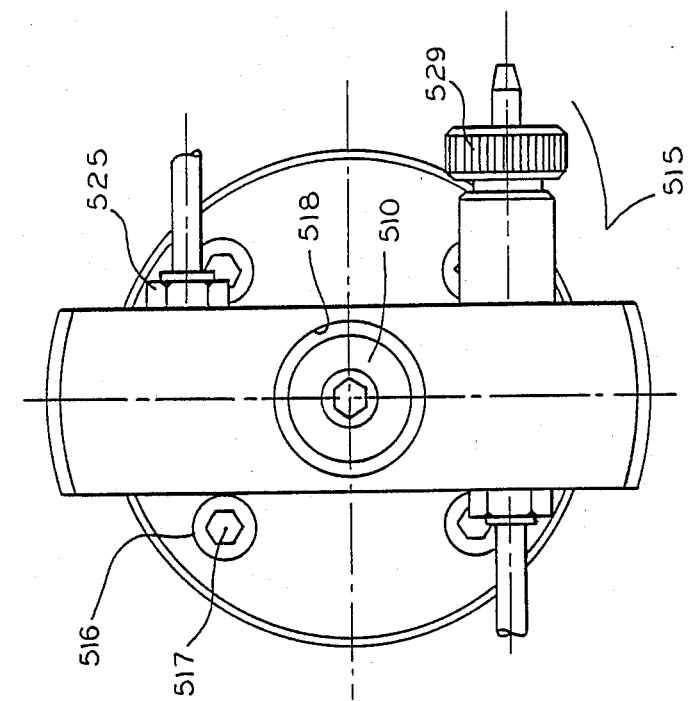
FIG. 7B is a front elevation thereof.
Figure 7A:
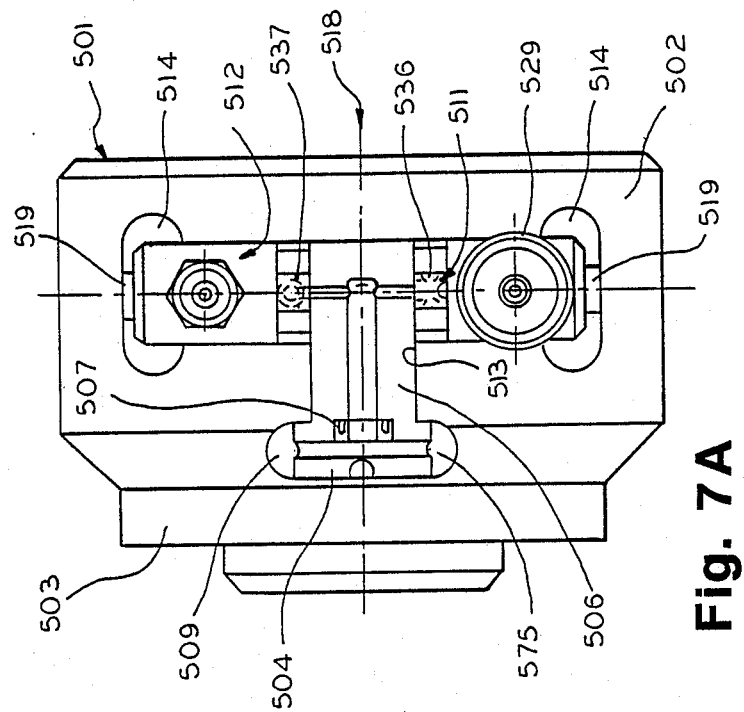
FIG. 7A is a side elevation of a fifth configuration of a small-size precision reciprocating metering pump.
Figures 9A, 9B:
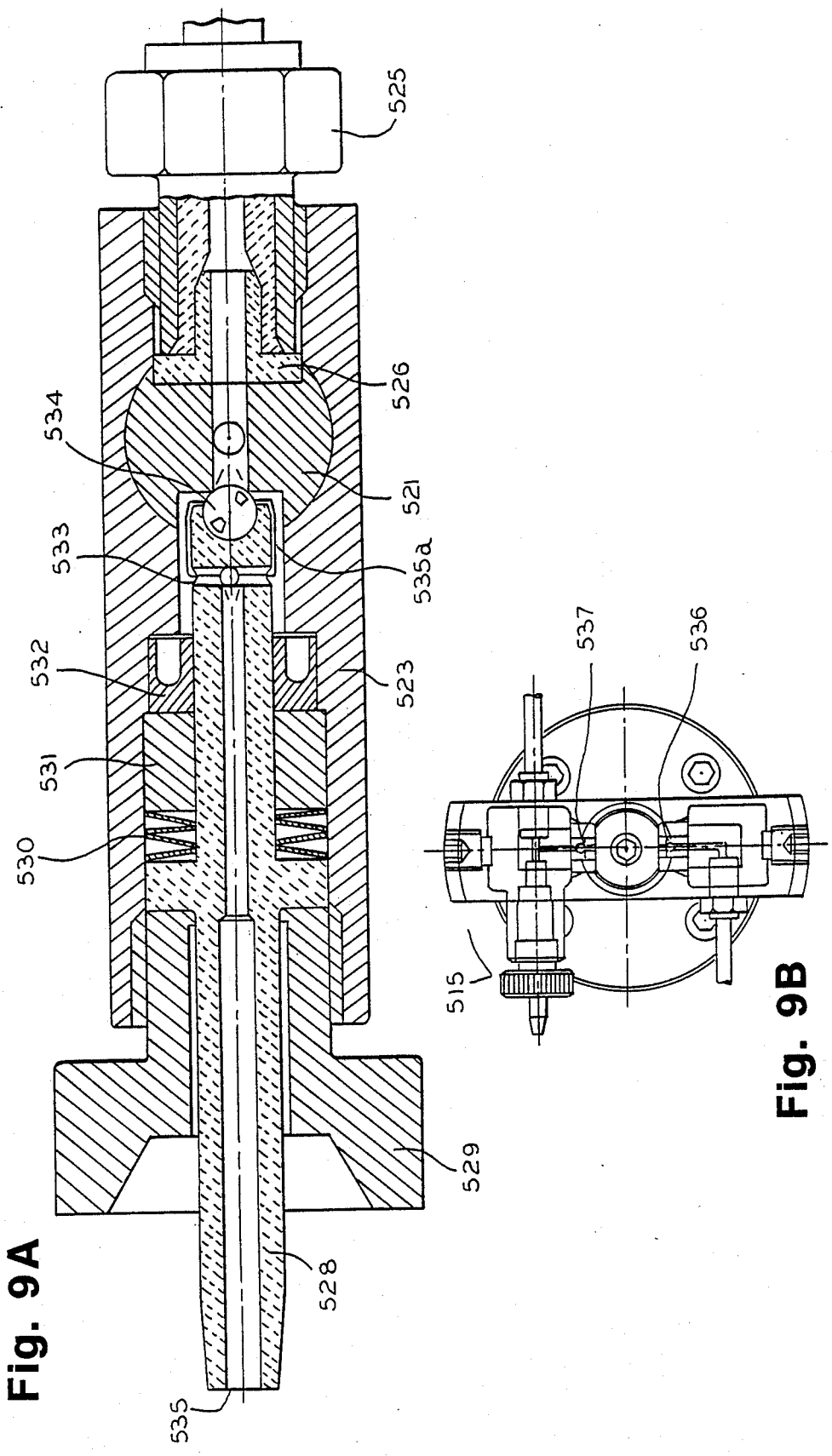
FIG. 9A is a longitudinal sectional view of a bleeder valve seen in FIG. 8B.
FIG. 9B is a view similar to FIG. 8B.

The separable tube line connections fitted to the check valve unit modules are of multi-adaptable design on the basis of a special fitting compression screw 525 (FIGS. 7B and 9A). Said screw features a bore which tapers at the end directed towards the tube end. High and low pressure connection can be performed using PTFE tubing or PTFE hose in conjunction with special polymer backing bushings 526 of T-shaped cross-section and by varying the bore diameter of the fitting compression screw 525. Also, conventional connections can be made using usual stainless steel capillary tubing together with a special ferrule 527, which is swaged onto the tubing as a mere retaining element, contrary to the usual mode, with its cone basis directed towards the tube end.

(3) The check valve unit modules optionally are fitted with an integrated bleeder-valve device 515 comprising a spring-washer 530, a knurled head-screw 529, a polymer bushing 531, and a guided spindle unit 528 as main functional components. This spindle unit is fitted on its delivery-flow wetted tip with a ruby ball 534, engaging as closing element into a mating bore in the check valve unit polymer liner 521,522. The spindle unit 528 further features a central liquid duct 535 for the waste flow. Said duct intersects with a cross-bore configuration 533 behind the closing ruby ball 534 crimped into the receiving bore of the tip of the spindle-unit, and by that, effects radial liquid connection with a collecting chamber 535a in the closing ruby ball area. This arm is sealed to the outside by an annular spring-loaded seal 532, when the bleeder-valve device is opened under the urging of spring 530 by loosening the pertinent knurled-head compression screw 529. Again, there is no contact with any metallic surface by the delivery flow of the liquid being pumped within the check valve unit module being modified as described.

The bleeder-valve integrated into said modified check valve unit module can be used as a port for priming the displacement system, when installed at the inlet side, or additionally as a venting port, when installed at the outlet side of the displacement system.

(4) Provision is made of special check valve cartridges 536,537 to be mounted into a recessed bore in the check valve unit module body 523,524. The flange of said receiving bore forms a crosswise slotted rim on the base of the module body 523,524. Internal sealing at the check valve cartridge/module body interface is effected by compression against the mating surface of the polymer cylinder 521,522 which lines the body of the check valve unit module 523,524. If necessary, however, an additional PTFE (FEP) film sealing gasket can be inserted.

With said check valve cartridges being based on the ball and seat-principle, ball 541 and seat 540 are fitted together with a ball guide element 542 featuring an integrated sieve-plate-like ball stopper end. These components are mounted in a thick-walled simple bushing-type housing 543 of sapphire and, in this case, polished on the inside and outside for transparency or, if transparency is not required, is made from zirconium oxide ceramic. The housing is thick-walled to withstand high pressure.

Since the check valve insert parts 540,541,542 are freely slidable within the pertinent housing 543, provision has to be made to prevent a falling-out during the procedure of assembling a check valve unit module. For retaining in the housing, the insert parts feature a small flat-ground section on their mantle surfaces leading to a small gap between the bore wall of the housing and the guide element 542, allowing the tight insertion of a micro-capillary PTFE tubing 545 after installation of the inner check valve cartridge components. Cut to the same length as the check valve cartridge housing 543, the tube segment drawn-through into the gap will secure the insert parts. Alternatively, a wetting of all components of the check valve cartridge will generate enough adhesion between each other to ensure securing during mounting.

I claim:

1. A precision reciprocating metering pump and control therefore comprising, a pump head casing with at least two displacement chambers having inlet and outlet ports, a piston for each displacement chamber, with at least one performing its displacement stroke at any given time whereby a pre-compression stroke is carried out prior to each such displacement stroke in order to compensate for the influence of the specific compressibility of the liquid being pumped on the pumping efficiency of the delivery system, a pair of check valve units associated with the inlet and outlet ports, at least one outlet check valve unit (28) comprising in part components made of transparent material, with a check valve ball (31) however, being colored or opaque, a piston position indicator and a sensor device monitoring the actual onset of the liquid displacement and connected to a piston speed control circuitry, whereby the underlying feed-back principle is characterized by said sensor device (111) monitoring the actual onset of the liquid displacement as triggered by the lifting of a check valve ball (31) from its seat (30) in at least one outlet check valve unit (28), and the sensor device (111) for monitoring the actual onset of liquid delivery, is an optical system, as for example, a light-gate, which is triggered by the lifting of the check valve ball (31) from its seat (30).

2. A precision reciprocating metering pump and control according to claim 1 characterized in that at least the housing of one outlet check valve unit (28) is made of sapphire or monocrystalline zirconium oxide and that the check valve ball (31) is of ruby.

3. A precision reciprocating metering pump and control therefore comprising, a pump head casing with at least two displacement chambers having inlet and outlet ports, a piston for each displacement chamber, with at least one performing its displacement stroke at any given time whereby a pre-compression stroke is carried out prior to each such displacement stroke in order to compensate for the influence of the specific compressibility of the liquid being pumped on the pumping efficiency of the delivery system, a pair of check valve units associated with the inlet and outlet ports, the check valve units having a ball engageable with a seat, a piston position indicator and a sensor device monitoring the actual onset of the liquid displacement and connected to a piston speed control circuitry, whereby the underlying feed-back principle is characterized by said sensor device monitoring the actual onset of the liquid displacement is triggered by the lifting of a check valve ball (31a) from its seat in at least one outlet check valve unit (28), and the check valve ball of at least one outlet check valve unit being made of ferro-magnetic material, preferably of stainless steel, and, the sensor device monitoring the actual onset of the liquid displacement senses magnetically the opening movement of the check valve ball.

4. A precision reciprocating metering pump and control according to claim 3 characterized in that the check valve ball of ferro-magnetic material is coated with a ceramic material, such as for example titanium carbide.

* * * * *